US010631721B2

(12) United States Patent
Kubo

(10) Patent No.: US 10,631,721 B2
(45) Date of Patent: Apr. 28, 2020

(54) LIVING BODY OBSERVATION SYSTEM

(71) Applicant: OLYMPUS CORPORATION, Tokyo (JP)

(72) Inventor: Kei Kubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/257,725

(22) Filed: Jan. 25, 2019

(65) Prior Publication Data
US 2019/0167086 A1 Jun. 6, 2019

Related U.S. Application Data

(63) Continuation of application No. PCT/JP2017/031746, filed on Sep. 4, 2017.

(30) Foreign Application Priority Data

Nov. 1, 2016 (JP) .................. 2016-214563

(51) Int. Cl.
A61B 1/06 (2006.01)
A61B 1/00 (2006.01)
(Continued)

(52) U.S. Cl.
CPC ........ *A61B 1/0661* (2013.01); *A61B 1/00006* (2013.01); *A61B 1/00009* (2013.01);
(Continued)

(58) Field of Classification Search
CPC . A61B 1/0661; A61B 1/00009; A61B 1/0684; A61B 1/0638; A61B 1/043;
(Continued)

(56) References Cited

U.S. PATENT DOCUMENTS

2010/0194871 A1 8/2010 Komukai
2013/0265401 A1* 10/2013 Igarashi ............... A61B 1/0661
348/68
(Continued)

FOREIGN PATENT DOCUMENTS

EP 2 213 222 A1 8/2010
JP 2010-172530 A 8/2010
(Continued)

OTHER PUBLICATIONS

International Search Report dated Oct. 24, 2017 received in PCT/JP2017/031746.

*Primary Examiner* — Shan E Elahi
(74) *Attorney, Agent, or Firm* — Scully, Scott, Murphy & Presser, P.C.

(57) ABSTRACT

A living body observation system has a light source apparatus configured to generate white observation light and excitation light for exciting fluorescent medical agent, a camera unit configured to pick up an image of a subject, a switch capable of giving an instruction to switch an observation mode, and a processor. The processor generates a white observation image and a fluorescent image; judges whether or not a parameter acquired based on the fluorescent image meets a condition under which observation of fluorescence is possible, switches to a fluorescence observation mode if the condition under which observation of the fluorescence is possible is met, when an instruction is given in a normal observation mode, and switches to a predetermined observation mode different from the fluorescence observation mode if the condition under which observation of the fluorescence is possible is not met.

9 Claims, 7 Drawing Sheets

(51) Int. Cl.
*A61B 1/04* (2006.01)
*A61B 1/055* (2006.01)
*A61B 5/00* (2006.01)
*A61B 1/045* (2006.01)

(52) U.S. Cl.
CPC ............ *A61B 1/043* (2013.01); *A61B 1/0638* (2013.01); *A61B 1/0684* (2013.01); *A61B 1/00096* (2013.01); *A61B 1/00186* (2013.01); *A61B 1/045* (2013.01); *A61B 1/055* (2013.01); *A61B 5/0084* (2013.01)

(58) Field of Classification Search
CPC . A61B 1/00006; A61B 1/00096; A61B 1/045; A61B 5/0084; A61B 1/00186; A61B 1/055
USPC .......................................................... 348/68
See application file for complete search history.

(56) References Cited

U.S. PATENT DOCUMENTS

2014/0071257 A1\* 3/2014 Yokota ............... A61B 1/00096
348/68
2016/0157763 A1\* 6/2016 Tominaga ............... A61B 1/043

FOREIGN PATENT DOCUMENTS

| JP | 2012-000160 A | 1/2012 |
| JP | 2012-152460 A | 8/2012 |
| JP | 2016-170182 A | 9/2016 |
| WO | 2015/012096 A1 | 1/2015 |

\* cited by examiner

LIVING BODY OBSERVATION SYSTEM

CROSS REFERENCE TO RELATED APPLICATION

This application is a continuation application of PCT/JP2017/031746 filed on Sep. 4, 2017 and claims benefit of Japanese Application No. 2016-214563 filed in Japan on Nov. 1, 2016, the entire contents of which are incorporated herein by this reference.

BACKGROUND OF THE INVENTION

1. Field of the Invention

The present invention relates to a living body observation system, and in particular to a living body observation system used for observation of living tissue.

2. Description of the Related Art

In endoscopic observation in a medical field, for example, normal observation capable of, by radiating white light to an object such as living tissue existing in a body cavity of a subject, causing an image with visibility almost similar to visibility when the object is seen by naked eyes to be displayed has been conventionally performed.

In the endoscopic observation in the medical field, for example, special light observation capable of, by radiating, to living tissue existing in a body cavity of a subject, special light which is light band-limited according to characteristics of a predetermined target object included in the living tissue, causing such an image that visibility of the predetermined target object is increased in comparison with the normal observation to be displayed has been conventionally performed.

Further, in the endoscopic observation in the medical field, a configuration has been conventionally proposed in which switching between a normal observation mode which is an operation mode for performing the normal observation described above and a special light observation mode which is an operation mode for performing the special light observation described above is possible.

More specifically, for example, Japanese Patent Application Laid-Open Publication No. 2012-160 discloses a configuration in which, in an endoscope apparatus, switching between a normal observation mode for performing observation by radiating white light to living tissue and a special light observation mode for performing observation by radiating narrowband light with a center wavelength of 405 nm to living tissue is possible. Further, Japanese Patent Application Laid-Open Publication No. 2012-160 discloses, as an example of PDD (photodynamic diagnosis), a method of observing fluorescence in a near infrared region emitted when excitation light with a center wavelength of 780 nm is radiated to ICG (indocyanine green) which is fluorescent medical agent.

Here, in a configuration in which switching among the normal observation mode and a plurality of special light observation modes including a fluorescence observation mode, which is an observation mode for performing fluorescent observation corresponding to PDD, is possible, it is desirable that switching among the respective observation modes is performed taking into account fading of fluorescence emitted from fluorescent medical agent administered to a subject and/or movement of the fluorescent medical agent administered to the subject and the like. Further, in the configuration in which switching among the normal observation mode and the plurality of special light observation modes is possible, it is desirable that an operation for switching among the respective observation modes is easy.

SUMMARY OF THE INVENTION

A living body observation system of one aspect of the present invention includes: a light source apparatus capable of generating white observation light for acquiring a white observation image of a subject and excitation light for exciting fluorescent medical agent administered to the subject as illumination light for illuminating the subject; a camera unit configured to pick up an image of the subject that the illumination light is radiated to; a switch for giving an instruction to switch an observation mode at the time of observing the subject to any one observation mode among a normal observation mode to display the white observation image as an observation image and a plurality of special light observation modes including a fluorescence observation mode to display an observation image generated using a fluorescent image of the subject; and a processor including hardware. The processor generates a white observation image of the subject that the white observation light is radiated to, the white observation image being picked up by the camera unit, and the fluorescent image of the subject that the excitation light is radiated to, the fluorescent image being picked up by the camera unit; the processor acquires a parameter corresponding to a light amount of fluorescence emitted from the fluorescent medical agent based on the fluorescent image and judges whether or not the parameter meets a condition under which observation of the fluorescence is possible; and, when the processor detects that the instruction is given in the normal observation mode, the processor performs an operation for switching to the fluorescence observation mode if it is judged by a judging portion that the parameter meets the condition under which observation of the fluorescence is possible, and performs an operation for switching to a predetermined observation mode different from the fluorescence observation mode, among the plurality of special light observation modes, if it is judged that the parameter does not meet the condition under which observation of the fluorescence is possible.

DETAILED DESCRIPTION OF THE PREFERRED EMBODIMENT

An embodiment of the present invention will be described below with reference to drawings.

FIGS. 1 to 9 relate to the embodiment of the present invention.

Figure 1:
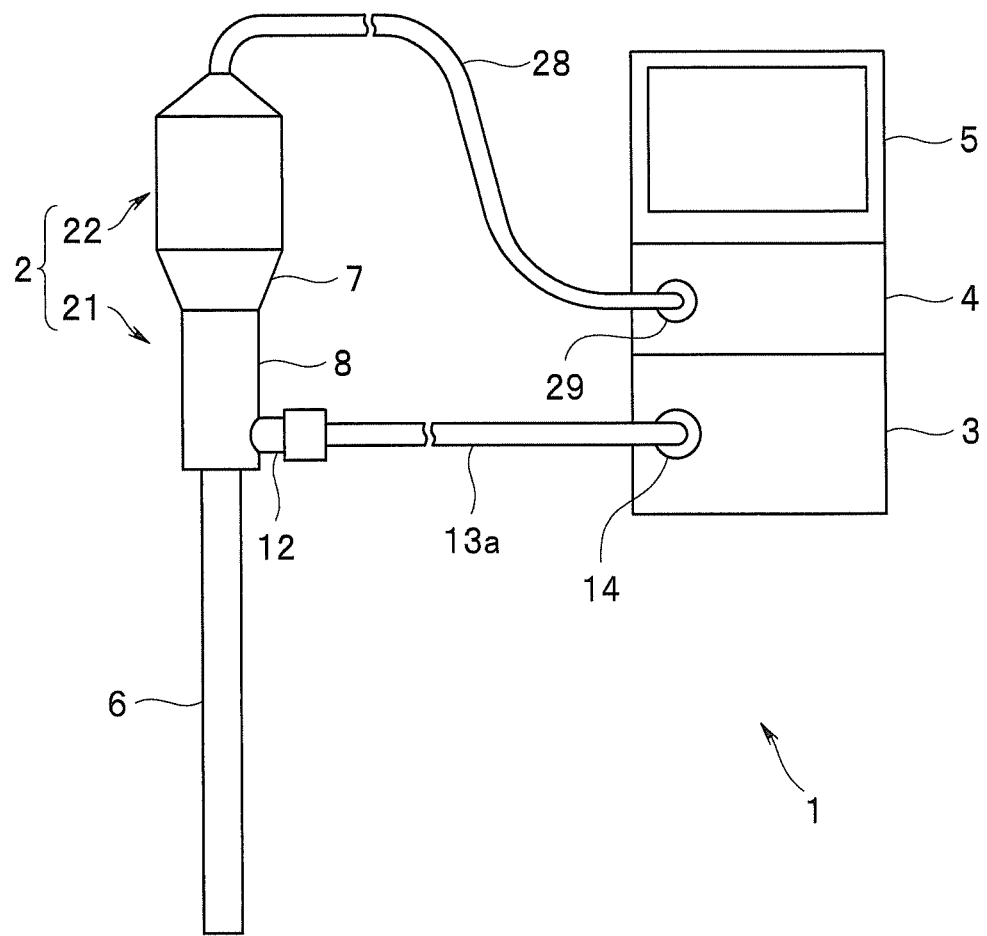
FIG. 1 is a diagram showing a configuration of main portions of a living body observation system according to an embodiment.

For example, as shown in FIG. 1, a living body observation system 1, which is an endoscope apparatus, has an endoscope 2 which is inserted into a subject and is configured to pick up an image of an object such as living tissue in the subject and output an image signal, a light source apparatus 3 configured to supply light, to be radiated to the object, to the endoscope 2, a processor 4 configured to generate and output an observation image based on the image signal outputted from the endoscope 2, and a display apparatus 5 configured to display the observation image outputted from the processor 4 on a screen. FIG. 1 is a diagram showing a configuration of main portions of a living body observation system according to the embodiment.

The endoscope 2 is configured having an optical viewing tube 21 provided with an elongated insertion portion 6, and a camera unit 22 attachable to and detachable from an eyepiece portion 7 of the optical viewing tube 21.

The optical viewing tube 21 is configured having the elongated insertion portion 6 which can be inserted into a subject, a grasping portion 8 provided at a proximal end portion of the insertion portion 6 and the eyepiece portion 7 provided at a proximal end portion of the grasping portion 8.

Figure 2:
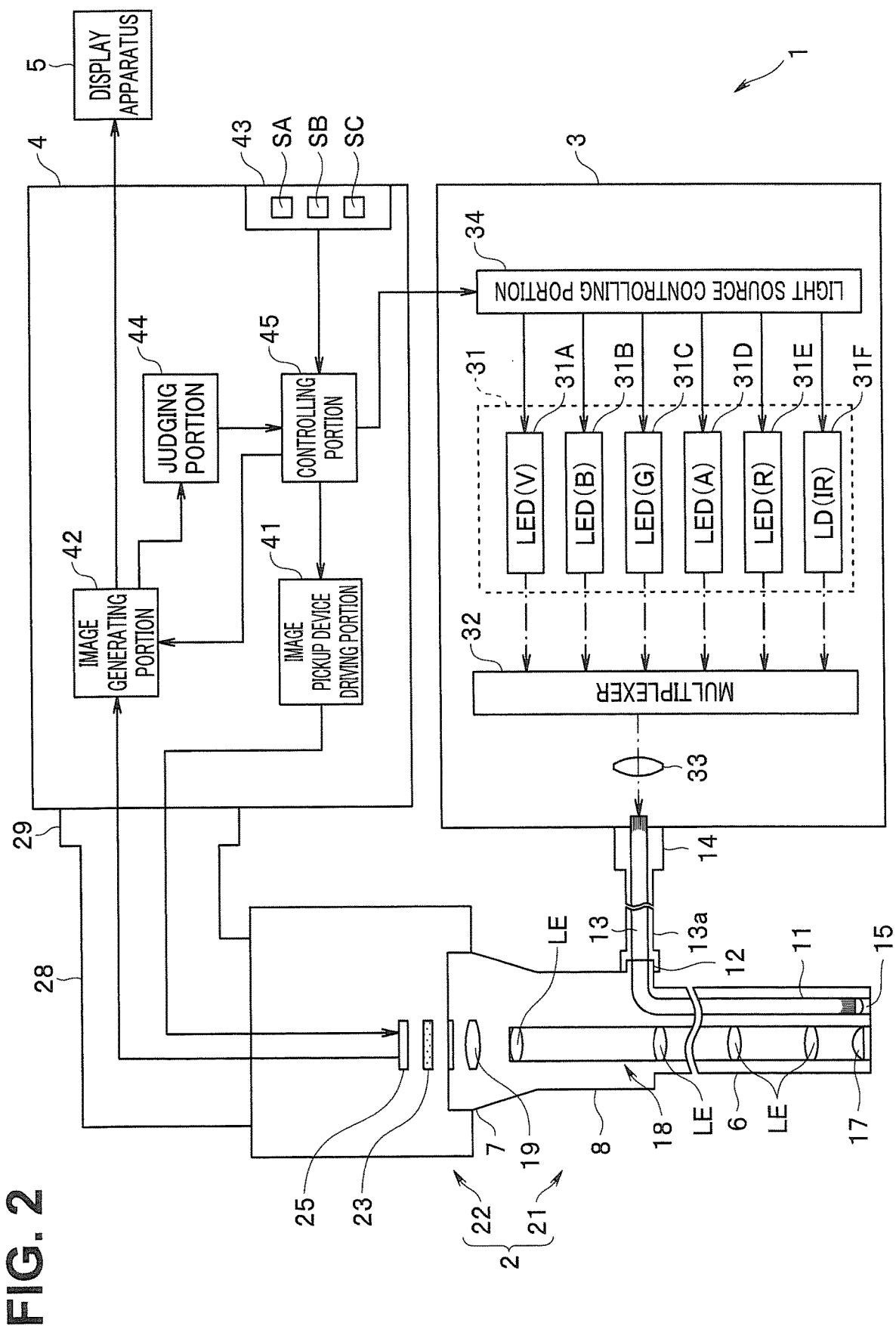
FIG. 2 is a diagram for illustrating an example of a specific configuration of the living body observation system according to the embodiment.

Inside the insertion portion 6, a light guide 11 for transmitting light supplied via a cable 13a is inserted as shown in FIG. 2. FIG. 2 is a diagram for illustrating an example of a specific configuration of the living body observation system according to the embodiment.

As shown in FIG. 2, an emission end portion of the light guide 11 is disposed near an illumination lens 15 on a distal end portion of the insertion portion 6. An incidence end portion of the light guide 11 is disposed on a light guide base 12 provided on the grasping portion 8.

Inside the cable 13a, a light guide 13 for transmitting light supplied from the light source apparatus 3 is inserted as shown in FIG. 2. On one end portion of the cable 13a, a connection member (not shown) attachable to and detachable from the light guide base 12 is provided. On the other end portion of the cable 13a, a light guide connector 14 attachable to and detachable from the light source apparatus 3 is provided.

On the distal end portion of the insertion portion 6, the illumination lens 15 for emitting light outside transmitted by the light guide 11 and an objective lens 17 for obtaining an optical image corresponding to light incident from outside are provided. On a distal end face of the insertion portion 6, an illumination window (not shown) in which the illumination lens 15 is disposed and an observation window (not shown) in which the objective lens 17 is disposed are provided, being adjacent to each other.

Inside the insertion portion 6, a relay lens 18 provided with a plurality of lenses LE for transmitting, to the eyepiece portion 7, an optical image obtained by the objective lens 17 is provided as shown in FIG. 2. That is, the relay lens 18 is configured being provided with a function as a transmission optical system for transmitting light incident from the objective lens 17.

Inside the eyepiece portion 7, an eyepiece lens 19 for making it possible to observe, by naked eyes, an optical image transmitted by the relay lens 18 is provided as shown in FIG. 2.

The camera unit 22 is configured being provided with a function as an image pickup portion. The camera unit 22 is configured having an excitation light cut filter 23 and an image pickup device 25. The camera unit 22 is configured having a signal cable 28 provided with a signal connector 29 attachable to and detachable from the processor 4, on an end portion.

Figure 3:
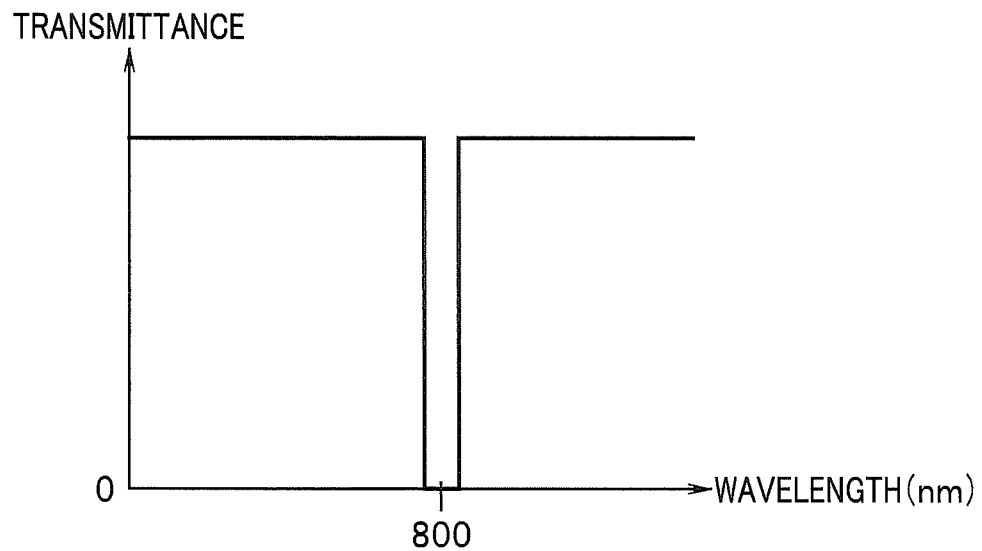
FIG. 3 is a diagram showing transmission characteristics as an example of optical characteristics of an excitation light cut filter provided in a camera unit of an endoscope according to the embodiment.

The excitation light cut filter 23 is disposed in front of the image pickup device 25 and is configured as an optical filter to remove reflected light of excitation light, from light emitted via the eyepiece lens 19. More specifically, for example, as shown in FIG. 3, the excitation light cut filter 23 is configured as an optical filter provided with optical characteristics of, among lights emitted via the eyepiece lens 19, blocking IR light (to be described later) the center wavelength of which is set to 800 nm while causing light other than the IR light to be transmitted. FIG. 3 is a diagram showing transmission characteristics as an example of optical characteristics of an excitation light cut filter provided in a camera unit of an endoscope according to the embodiment.

Figure 4:
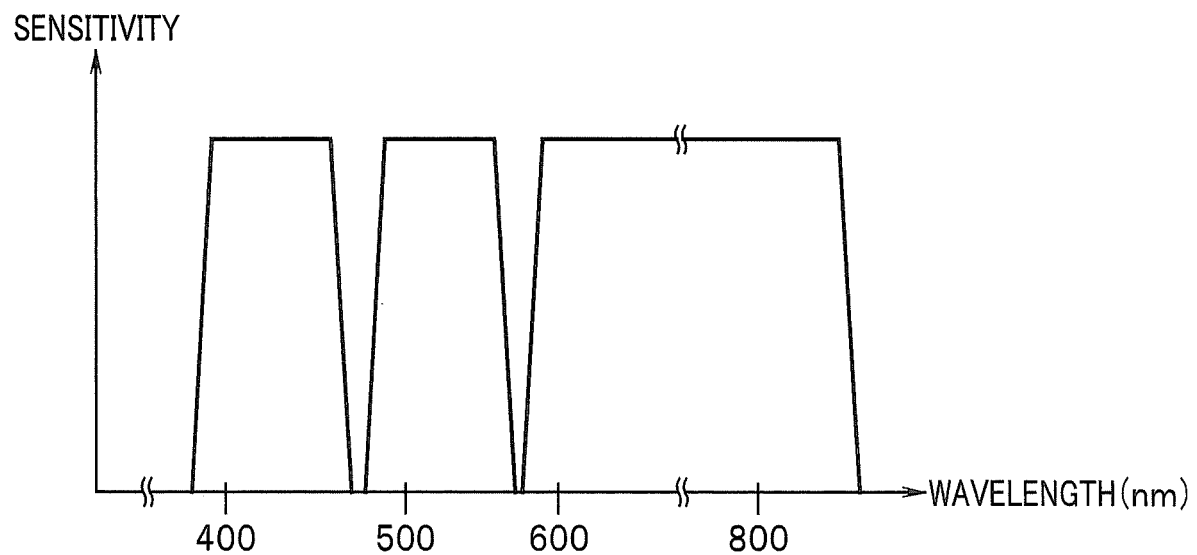
FIG. 4 is a diagram showing an example of sensitivity characteristics of an image pickup device provided in the camera unit of the endoscope according to the embodiment.

The image pickup device 25 is configured, for example, being provided with a color CMOS image sensor. The image pickup device 25 is disposed at a position making it possible to receive light transmitted through the excitation light cut filter 23, inside the camera unit 22. The image pickup device 25 is configured being provided with a plurality of pixels for performing photoelectric conversion of light transmitted through the excitation light cut filter 23 to perform image pickup, and a primary color filter provided on an image pickup surface where the plurality of pixels are two-dimensionally arranged. The image pickup device 25 is configured to be driven in response to an image pickup device driving signal outputted from the processor 4. The image pickup device 25 is configured, for example, being provided with sensitivity characteristics as illustrated in FIG. 4. That is, on the image pickup surface of the image pickup device 25, a plurality of B pixels having sensitivity in a blue region including wavelength bands of V light and B light, which will be described later, a plurality of G pixels having sensitivity in a green region including a wavelength band of G light, which will be described later, and a plurality of R pixels having sensitivity in red to near infrared regions including wavelength bands of A light, R light, IR light and FL light, which will be described later, are provided, respectively. FIG. 4 is a diagram showing an example of sensitivity characteristics of an image pickup device provided in the camera unit of the endoscope according to the embodiment.

The image pickup device 25 is configured to generate an image pickup signal by picking up an image of light transmitted through the excitation light cut filter 23 and output the generated image pickup signal to the processor 4 to which the signal cable 28 is connected.

For example, as shown in FIG. 2, the light source apparatus 3 is configured having a light emitting portion 31, a multiplexer 32, a condenser lens 33 and a light source controlling portion 34.

The light emitting portion 31 is configured having an LED (light-emitting diode) 31A, an LED 31B, an LED 31C, an LED 31D, an LED 31E and an LD (laser diode) 31F.

Figure 5:
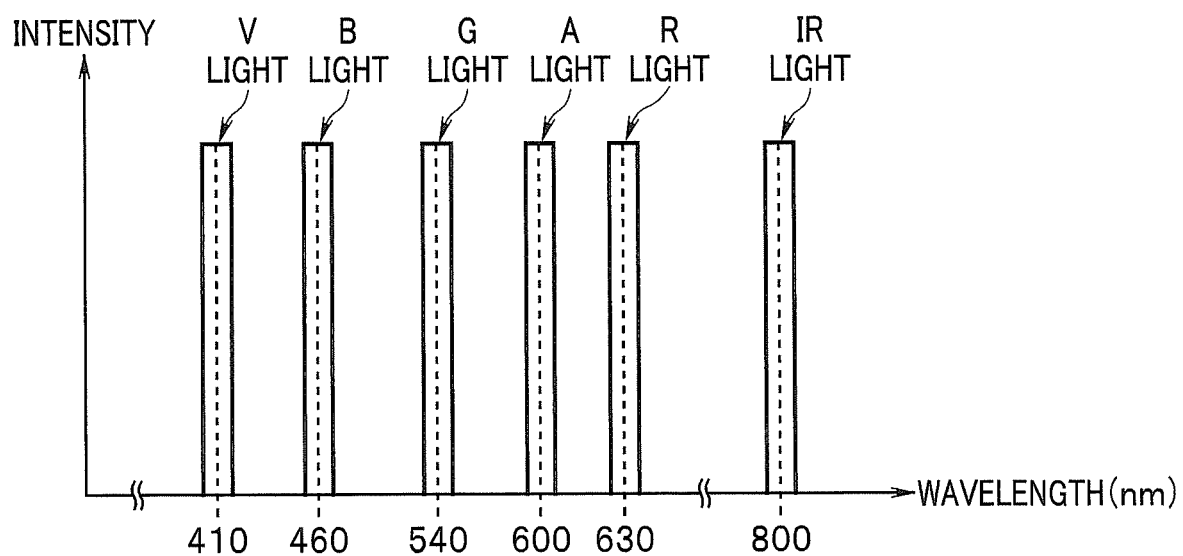
FIG. 5 is a diagram showing an example of light emitted from a light source apparatus according to the embodiment.

For example, as shown in FIG. 5, a center wavelength of the LED 31A is set to 410 nm, and the LED 31A is configured to emit V light which is narrowband light belonging to the blue region. The LED 31A is configured to be switched to a light-up state or a light-out state according to control of the light source controlling portion 34. The LED 31A is configured to generate V light with an intensity according to control of the light source controlling portion 34 in the light-up state. FIG. 5 is a diagram showing an example of light emitted from a light source apparatus according to the embodiment.

For example, as shown in FIG. 5, a center wavelength of the LED 31B is set to 460 nm, and the LED 31B is configured to emit B light which is narrowband light belonging to the blue region. The LED 31B is configured to be switched to the light-up state or the light-out state according to control of the light source controlling portion 34. The LED 31B is configured to generate B light with an intensity according to control of the light source controlling portion 34 in the light-up state.

For example, as shown in FIG. 5, a center wavelength of the LED 31C is set to 540 nm, and the LED 31C is configured to emit the G light which is narrowband light belonging to the green region. The LED 31C is configured to be switched to the light-up state or the light-out state according to control of the light source controlling portion 34. The LED 31C is configured to generate G light with an intensity according to control of the light source controlling portion 34 in the light-up state.

For example, as shown in FIG. 5, a center wavelength of the LED 31D is set to 600 nm, and the LED 31D is configured to emit A light which is narrowband light belonging to the red region. The LED 31D is configured to be switched to the light-up state or the light-out state according to control of the light source controlling portion 34. The LED 31D is configured to generate A light with an intensity according to control of the light source controlling portion 34 in the light-up state.

For example, as shown in FIG. 5, a center wavelength of the LED 31E is set to 630 nm, and the LED 31E is configured to emit R light which is narrowband light belonging to the red region. The LED 31E is configured to be switched to the light-up state or the light-out state according to control of the light source controlling portion 34. The LED 31E is configured to generate R light with an intensity according to control of the light source controlling portion 34 in the light-up state.

For example, as shown in FIG. 5, a center wavelength of the LD 31F is set to 800 nm, and the LD 31F is configured to emit IR light which is narrowband light belonging to the near infrared region. The LD 31F is configured to be switched to the light-up state or the light-out state according to control of the light source controlling portion 34. The LD 31F is configured to generate IR light with an intensity according to control of the light source controlling portion 34 in the light-up state.

The multiplexer 32 is configured to be capable of multiplexing respective lights generated from the light emitting portion 31 and cause the multiplexed light to be incident to the condenser lens 33.

The condenser lens 33 is configured to condense light incident via the multiplexer 32 and emit the light to the light guide 13.

The light source controlling portion 34 is configured, for example, being provided with a light source controlling circuit and the like. The light source controlling portion 34 is configured to perform control for each light source of the light emitting portion 31 based on a system control signal outputted from the processor 4.

That is, the light source apparatus 3 is provided with a function as a light source portion and is configured to generate white light (white observation light) for illuminating a subject, for example, by multiplexing V light, B light, G light and R light simultaneously emitted from the light emitting portion 31 by the multiplexer 32. The light source apparatus 3 is configured to generate the IR light as excitation light for exciting fluorescent medical agent administered to a subject as described later.

For example, as shown in FIG. 2, the processor 4 is configured having an image pickup device driving portion 41, an image generating portion 42, an input I/F (interface) 43, a judging portion 44 and a controlling portion 45.

The image pickup device driving portion 41 is configured, for example, being provided with a driver circuit and the like. The image pickup device driving portion 41 is configured to generate and output an image pickup device driving signal for causing the image pickup device 25 to be driven, based on a system control signal outputted from the controlling portion 45.

The image generating portion 42 is configured, for example, being provided with an image generating circuit and the like. The image generating portion 42 is configured to generate an image corresponding to light image-picked up by the image pickup device 25, based on an image pickup signal outputted from the endoscope 2 and a system control signal outputted from the controlling portion 45. The image generating portion 42 is configured to output a fluorescent image generated according to fluorescence image-picked up by the image pickup device 25, to the judging portion 44 based on a system control signal outputted from the controlling portion 45. The image generating portion 42 is configured to generate an observation image corresponding to an observation mode of the living body observation system 1 and output the observation image to the display apparatus 5, based on a system control signal outputted from the controlling portion 45.

The input I/F 43 is configured being provided with a switch capable of giving an instruction or the like corresponding to a user operation. More specifically, the input I/F 43 is provided with an observation starting switch SA (hereinafter also referred to simply as a switch SA) configured as a single push-button switch capable of giving an instruction to the effect that observation of a subject by the living body observation system 1 is to be started, to the controlling portion 45 in response to pressing by a user. The input I/F 43 is provided with an observation mode switching switch SB (hereinafter also referred to simply as a switch SB) configured as a single push-button switch capable of giving an instruction to switch an observation mode at the time of performing observation of a subject by the living body observation system 1 to any one observation mode among the normal observation mode and the plurality of special light observation modes, in response to pressing by the user. The input I/F 43 is provided with an observation ending switch SC (hereinafter also referred to simply as a switch SC) configured as a single push-button switch capable of giving an instruction, to the controlling portion 45, to the effect that observation of a subject by the living body observation system 1 is to be ended, in response to pressing by the user.

The judging portion 44 is configured, for example, being provided with a judging circuit and the like. The judging portion 44 is configured to perform a process for acquiring a predetermined parameter corresponding to the light amount of fluorescence emitted from fluorescent medical agent administered to a subject, based on a fluorescent image outputted from the image generating portion 42. The judging portion 44 is configured to perform a judgment process for judging whether the predetermined parameter acquired as described above meets a predetermined condition or not. The judging portion 44 is configured to output a judgment result obtained by the judgment process described above to the controlling portion 45.

The controlling portion 45 is configured, for example, being provided with a controlling circuit such as a CPU, or an FPGA (field programmable gate array) or the like. The controlling portion 45 is configured to, when the controlling portion 45 detects that an instruction in response to pressing of the switch SA has been given, set the observation mode of the living body observation system 1 to the normal observation mode, generate a system control signal for causing an operation corresponding to the normal observation mode to be performed, and output the generated system control signal to the light source controlling portion 34, the image pickup device driving portion 41 and the image generating portion 42. The controlling portion 45 is configured to, when the controlling portion 45 detects that an instruction in response to pressing of the switch SB has been given after detecting the instruction in response to pressing of the switch SA, perform an operation for setting the observation mode of the living body observation system 1 to any one observation mode among the normal observation mode and the plurality of special light observation modes, based on a judgment result or the like outputted from the judging portion 44. The controlling portion 45 is configured to generate a system control signal for causing an operation corresponding to a set observation mode to be performed and output the generated system control signal to the light source controlling portion 34, the image pickup device driving portion 41 and the image generating portion 42, as described above. The controlling portion 45 is configured to, when the controlling portion 45 detects that an instruction in response to pressing of the switch SC has been performed, generate a system control signal for stopping supply of light to the endoscope 2 and image pickup of a subject by the endoscope 2 and output the generated system control signal to the light source controlling portion 34 and the image pickup device driving portion 41.

The display apparatus 5 is provided with, for example, an LCD (liquid crystal display) and the like and is configured to be capable of displaying an observation image and the like outputted from the processor 4.

Next, operations and the like of the living body observation system 1 of the present embodiment will be described. Note that, hereinafter, description will be made on a case where the plurality of special light observation modes switchable in response to an instruction given in response to pressing of the switch SB are two modes, that is, a fluorescence observation mode and a deep blood vessel observation mode, as an example. Further, hereinafter, description will be made on a case where, in a state in which fluorescent medical agent such as indocyanine green is administered to a subject, the fluorescent medical agent being excited by radiation of the IR light, which is excitation light, and generating FL light, which is fluorescence in the near infrared region with a wavelength longer than a wavelength of the IR light, a desired object existing in a body cavity of the subject is observed, as an example.

A user who is a surgeon or the like connects each portion of the living body observation system 1 and powers on the living body observation system 1, and after that, gives an instruction to the effect that observation by the living body observation system 1 is to be started, by pressing the switch SA of the input I/F 43.

When the controlling portion 45 detects that the instruction in response to pressing of the switch SA of the input I/F 43 has been given, the controlling portion 45 sets the observation mode of the living body observation system 1 to the normal observation mode, generates a system control signal for causing the operation corresponding to the normal observation mode to be performed, and outputs the generated system control signal to the light source controlling portion 34, the image pickup device driving portion 41 and the image generating portion 42.

Based on the system control signal outputted from the controlling portion 45, the light source controlling portion 34 controls the light emitting portion 31 to cause the LED 31D and the LD 31F to be extinguished while simultaneously causing the LEDs 31A, 31B, 31C and 31E to light up.

That is, according to the operation of the light source controlling portion 34 described above, when the observation mode of the living body observation system 1 is set to the normal observation mode, WL light, which is white light (white observation light) obtained by multiplexing V light, B light, G light and R light by the multiplexer 32, is supplied from the light source apparatus 3 to the light guide 13 of the endoscope 2, and the WL light is radiated to the desired object in the subject. When the observation mode of the living body observation system 1 is set to the normal observation mode, WR light, which is reflected light of the WL light radiated to the object, is caused to be incident from the objective lens 17 as return light, and the WR light is transmitted through the excitation light cut filter 23 and reaches the image pickup surface of the image pickup device 25. Note that, in the present embodiment, in a case where the image pickup device 25 is a monochrome image pickup device having sensitivity at least in a visible region to the near infrared region, the light source controlling portion 34 may control the light emitting portion 31 to perform radiation of V light and B light, radiation of G light and radiation of R light by time division to generate a blue observation image, a green observation image and a red observation image for generating a white observation image.

The image pickup device 25 generates an image pickup signal by picking up an image of the WR light transmitted through the excitation light cut filter 23 and outputs the generated image pickup signal to the processor 4.

That is, according to the operation of the image pickup device 25 described above, the V light and the B light included in the WR light transmitted through the excitation light cut filter 23 are image-picked up by the B pixels, the G light included in the WR light is image-picked up by the G pixels, and the R light included in the WR light is image-picked up by the R pixels.

The image generating portion 42 generates a normal observation image corresponding to the WR light image-picked up by the image pickup device 25, based on the image pickup signal outputted from the endoscope 2 and a system control signal outputted from the controlling portion 45. The image generating portion 42 outputs the normal observation image to the display apparatus 5 as an observation image based on a system control signal outputted from the controlling portion 45.

That is, according to the operation of the image generating portion 42 as described above, when the observation mode of the living body observation system 1 is set to the normal observation mode, for example, a normal observation image provided with color tone almost similar to color tone when living tissue or the like in the subject is seen by naked eyes is displayed on the display apparatus 5 as an observation image.

The user inserts the insertion portion 6 into the subject while confirming the normal observation image displayed on the display apparatus 5. Then, in a state in which the distal end portion of the insertion portion 6 is disposed near the desired object existing in the subject, the user observes the desired object while pressing the switch SB of the input I/F 43 at an appropriate timing.

Figure 6:
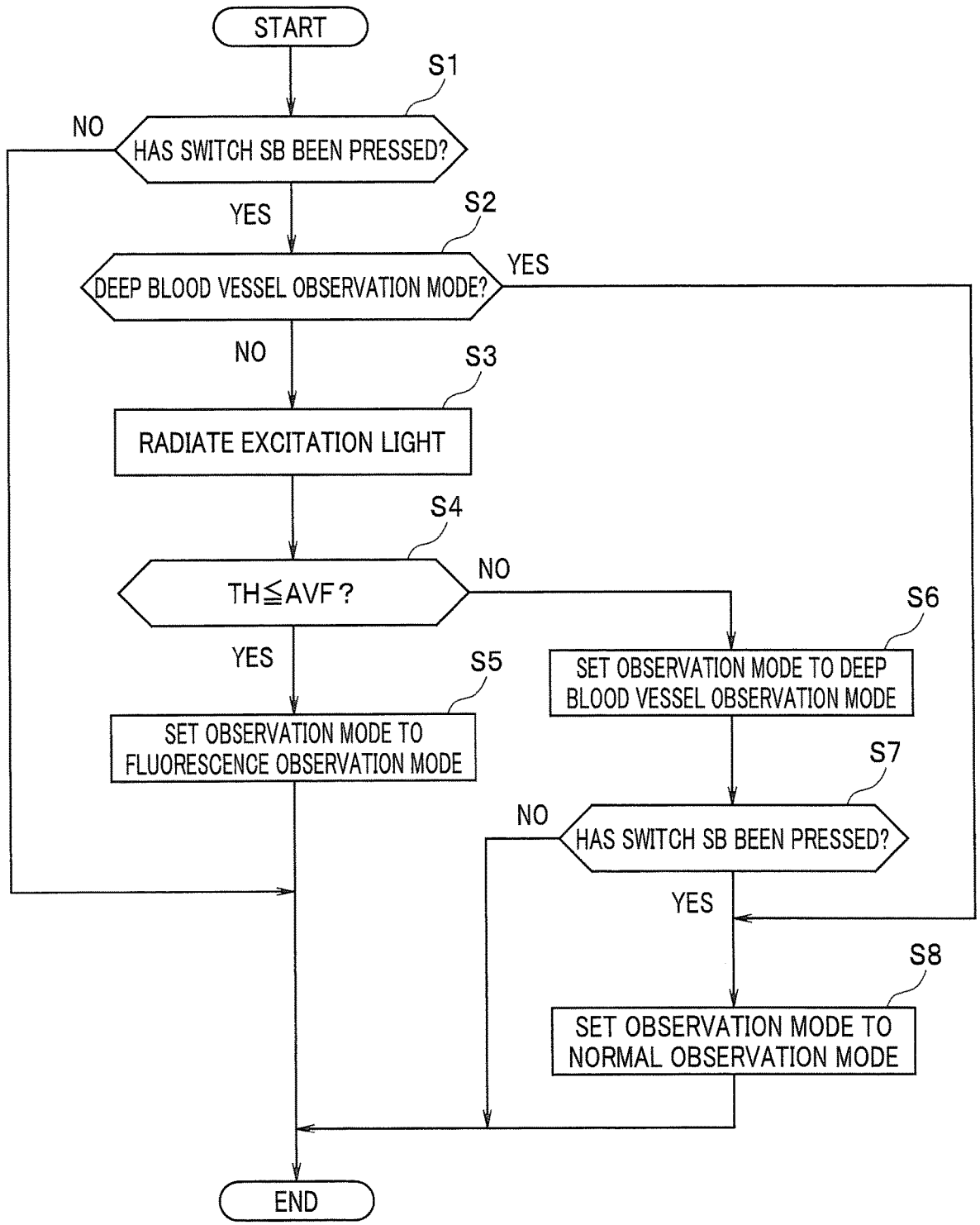
FIG. 6 is a flowchart for illustrating a specific example of an operation performed in the living body observation system according to the embodiment.

Here, a specific example of an operation and the like for setting of an observation mode performed in response to pressing of the switch SB will be described with reference to FIG. 6. FIG. 6 is a flowchart for illustrating a specific example of an operation performed in the living body observation system according to the embodiment.

The controlling portion 45 performs an operation for detecting the instruction in response to pressing of the switch SB (step S1 of FIG. 6).

If the controlling portion 45 cannot detect the instruction in response to pressing of the switch SB at step S1 of FIG. 6 (S1: NO), the controlling portion 45 maintains an observation mode set currently. If the controlling portion 45 can detect the instruction in response to pressing of the switch SB at step S1 of FIG. 6 (S1: YES), the controlling portion 45 performs a judgment process about whether the observation mode set currently is the deep blood vessel observation mode or not (step S2 of FIG. 6).

If the controlling portion 45 obtains a judgment result that the observation mode set currently is the deep blood vessel observation mode at step S2 of FIG. 6 (S2: YES), the controlling portion 45 subsequently performs a process of step S8 of FIG. 6, which will be described later. If the controlling portion 45 obtains a judgment result that the observation mode set currently is not the deep blood vessel observation mode at step S2 of FIG. 6 (S2: NO), that is, if the controlling portion 45 obtains a judgment result that the observation mode set currently is either the normal observation mode or the fluorescence observation mode, the controlling portion 45 generates a system control signal for causing excitation light in a predetermined light amount PA to be radiated during a predetermined time period PT and outputs the system control signal to the light source controlling portion 34 (S3 of FIG. 6).

More specifically, at step S3 of FIG. 6, the controlling portion 45 generates a system control signal, for example, for causing WL light and IR light in a predetermined light amount PA to be generated only during the predetermined time period PT by time division or alternately and outputs the system control signal to the light source controlling portion 34.

Along with the operation of step S3 of FIG. 6, the controlling portion 45 generates a system control signal for causing a fluorescent image generated during the predetermined time period PT to be outputted to the judging portion 44 and outputs the system control signal to the image generating portion 42.

According to the operation of the controlling portion 45 as described above, during a period until the predetermined time period PT elapses after the operation of step S3 of FIG. 6 is started, the WL light and the IR light are radiated to the desired object in the subject by time division or alternately, and WR light which is reflected light of the WL light, FL light which is fluorescence emitted from the fluorescent medical agent excited by radiation of the IR light, and reflected light of the IR light are sequentially caused to be incident from the objective lens 17 as return light. According to the operation of the controlling portion 45 as described above, during the period until the predetermined time period PT elapses after the control of step S3 of FIG. 6 is started, each of the WR light and the FL light transmitted through the excitation light cut filter 23 is image-picked up by the image pickup device 25, and each of a normal observation image corresponding to the WR light and a fluorescent image corresponding to the FL light is generated by the image generating portion 42, and the fluorescent image is outputted to the judging portion 44.

Based on the fluorescent image outputted from the image generating portion 42 during the period until the predetermined time period PT elapses after the operation of step S3 of FIG. 6 is started, the judging portion 44 performs a process for acquiring an average brightness value AVF of the fluorescent image as a predetermined parameter corresponding to the light amount of the FL light (fluorescence) emitted from the fluorescent medical agent administered to the subject. Then, the judging portion 44 performs a judgment process about whether or not the average brightness value AVF acquired as described above is equal to or above a predetermined threshold THA (step S4 of FIG. 6) and outputs a judgment result obtained by the judgment process to the controlling portion 45. That is, at step S4 of FIG. 6, the judging portion 44 performs a judgment process for judging whether or not the average brightness value AVF of the fluorescent image meets a condition under which observation of fluorescence is possible.

If a judgment result that the average brightness value AVF is equal to or above the predetermined threshold THA (S4: YES) is obtained, based on the judgment result outputted from the judging portion 44, the controlling portion 45 sets the observation mode of the living body observation system 1 to the fluorescence observation mode (step S5 of FIG. 6), generates a system control signal for causing an operation corresponding to the fluorescence observation mode to be performed, and outputs the generated system control signal to the light source controlling portion 34, the image pickup device driving portion 41 and the image generating portion 42. That is, if a judgment result showing that observation of the FL light emitted from the fluorescent medical agent administered to the subject is possible is obtained, based on the judgment result outputted from the judging portion 44, the controlling portion 45 performs an operation for switching the observation mode of the living body observation system 1 to the fluorescence observation mode.

Based on the system control signal outputted from the controlling portion 45, the light source controlling portion 34 controls the light emitting portion 31 to cause the LED 31D and the LD 31F to be extinguished while causing the LEDs 31A, 31B, 31C and 31E to light up and controls the light emitting portion 31 to cause the LD 31F to light up while causing the LEDs 31A to 31E to be extinguished, alternately.

That is, according to the operation of the light source controlling portion 34 as described above, when the observation mode of the living body observation system 1 is set to the fluorescence observation mode, WL light and IR light are supplied to the light guide 13 of the endoscope 2 from the light source apparatus 3 by time division or alternately, and the WL light and the IR light are radiated to the desired object in the subject by time division or alternately. When the observation mode of the living body observation system 1 is set to the fluorescence observation mode, WR light, FL light and reflected light of the IR light are caused to be incident from the objective lens 17 as return light, and the WR light and the FL light are transmitted through the excitation light cut filter 23 and sequentially reach the image pickup surface of the image pickup device 25.

Note that, in the present embodiment, the light amount of the IR light supplied to the endoscope 2 from the light source apparatus 3 in the fluorescence observation mode may be different from the predetermined light amount PA or may be the same as the predetermined light amount PA.

The image pickup device 25 generates an image pickup signal by picking up an image of each of the WR light and the FL light transmitted through the excitation light cut filter 23 and outputs the generated image pickup signal to the processor 4.

That is, according to the operation of the image pickup device 25 as described above, V light and B light included in the WR light transmitted through the excitation light cut filter 23 are image-picked up by the B pixels, G light included in the WR light is image-picked up by the G pixels, and R light included in the WR light is image-picked up by the R pixels. According to the operation of the image pickup device 25 as described above, the FL light transmitted through the excitation light cut filter 23 is image-picked up by the R pixels.

Based on the image pickup signals outputted from the endoscope 2 and a system control signal outputted from the controlling portion 45, the image generating portion 42 generates a normal observation image corresponding to the WR light image-picked up by the image pickup device 25 and a fluorescent image corresponding to the FL light image-picked up by the image pickup device 25, respectively. Further, based on a system control signal outputted from the controlling portion 45, the image generating portion 42 generates an observation image using the normal observation image and the fluorescent image and outputs the generated observation image to the display apparatus 5.

That is, according to the operation of the image generating portion 42 as described above, when the observation mode of the living body observation system 1 is set to the fluorescence observation mode, for example, such an image that information showing a position of generation of FL light emitted from the fluorescent medical agent accumulated on a lesion in the subject is added to (overlapped on) a normal observation image is displayed on the display apparatus 5 as an observation image.

Note that, according to the present embodiment, as far as an observation image which is a fluorescent image is generated and displayed in the fluorescence observation mode, an observation image different from the observation image described above may be generated and displayed in the fluorescence observation mode.

On the other hand, if a judgment result that the average brightness value AVF is below the predetermined threshold THA is obtained (S4: NO), based on the judgment result outputted from the judging portion 44, the controlling portion 45 sets the observation mode of the living body observation system 1 to the deep blood vessel observation mode (step S6 of FIG. 6), generates a system control signal for causing an operation corresponding to the deep blood vessel observation mode to be performed, and outputs the generated system control signal to the light source controlling portion 34, the image pickup device driving portion 41 and the image generating portion 42. That is, if a judgment result showing that observation of the FL light emitted from the fluorescent medical agent administered to the subject is impossible is obtained, based on the judgment result outputted from the judging portion 44, the controlling portion 45 performs an operation for switching the observation mode of the living body observation system 1 to the deep blood vessel observation mode.

Based on the system control signal outputted from the controlling portion 45, the light source controlling portion 34 controls the light emitting portion 31 to cause the LEDs 31A, 31C, 31D and the LD 31F to be extinguished while causing the LEDs 31B and 31E to light up and controls the light emitting portion 31 to cause the LEDs 31A, 31B, 31C and 31E and the LD 31F to be extinguished while causing the LED 31D to light up, alternately.

That is, according to the operation of the light source controlling portion 34 as described above, when the observation mode of the living body observation system 1 is set to the deep blood vessel observation mode, ML light, which is mixed light obtained by multiplexing B light and R light by the multiplexer 32, and A light are supplied to the light guide 13 of the endoscope 2 from the light source apparatus 3 by time division or alternately, and the ML light and the A light are radiated to the desired object in the subject by time division or alternately. When the observation mode of the living body observation system 1 is set to the deep blood vessel observation mode, MR light, which is reflected light of the ML light radiated to the object, and AR light, which is reflected light of the A light radiated to the object, are caused to be incident from the objective lens 17 as return light, and the MR light and the AR light are transmitted through the excitation light cut filter 23 and sequentially reach the image pickup surface of the image pickup device 25.

The image pickup device 25 generates an image pickup signal by picking up an image of each of the MR light and the AR light transmitted through the excitation light cut filter 23 and outputs the generated image pickup signal to the processor 4.

That is, according to the operation of the image pickup device 25 as described above, the B light included in the MR light transmitted through the excitation light cut filter 23 is image-picked up by the B pixels, and the R light included in the MR light is image-picked up by the R pixels. According to the operation of the image pickup device 25 as described above, the AR light transmitted through the excitation light cut filter 23 is image-picked up by the R pixels.

Based on the image pickup signals outputted from the endoscope 2 and a system control signal outputted from the controlling portion 45, the image generating portion 42 generates a blue light image corresponding to the B light included in the MR light image-picked up by the image pickup device 25, a red light image corresponding to the R light included in the MR light, and an amber light image corresponding to the AR light image-picked up by the image pickup device 25, respectively. Further, based on a system control signal outputted from the controlling portion 45, the image generating portion 42 generates an observation image using the blue light image, the amber light image and the red light image and outputs the generated observation image to the display apparatus 5.

That is, according to the operation of the image generating portion 42 as described above, when the observation mode of the living body observation system 1 is set to the deep blood vessel observation mode, for example, an image in which a large-diameter blood vessel existing in the depth of the desired object in the subject is emphasized is displayed on the display apparatus 5 as an observation image.

After completing the operation of step S6 of FIG. 6, the controlling portion 45 performs the operation for detecting the instruction in response to pressing of the switch SB (step S7 of FIG. 6).

If the controlling portion 45 cannot detect the instruction in response to pressing of the switch SB at step S7 of FIG. 6 (S7: NO), the controlling portion 45 maintains the deep blood vessel observation mode set by the operation of step S6 of FIG. 6. In a case where the instruction in response to pressing of the switch SB can be detected at step S7 of FIG. 6 (S7: YES), the controlling portion 45 sets the observation mode of the living body observation system 1 to the normal observation mode (step S8 of FIG. 6), generates a system control signal for causing an operation corresponding to the normal observation mode to be performed, and outputs the generated system control signal to the light source controlling portion 34, the image pickup device driving portion 41 and the image generating portion 42.

Then, by repeatedly performing the series of operations in FIG. 6 during a period until the switch SC is pressed after the switch SA is pressed, the controlling portion 45 sets the observation mode of the living body observation system 1 to any one observation mode among the normal observation mode, the fluorescence observation mode and the deep blood vessel observation mode.

As described above, according to the present embodiment, the observation mode of the living body observation system 1 is prevented from being switched to the fluorescence observation mode when it is judged that observation of fluorescence emitted from the fluorescent medical agent administered to the subject is impossible. That is, according to the present embodiment, for example, in a case where fluorescence emitted from the fluorescent medical agent administered to the subject almost completely fades away, and/or in a case where the fluorescent medical agent is almost completely excreted by metabolism, the observation mode of the living body observation system 1 is prevented from being switched to the fluorescence observation mode. As described above, according to the present embodiment, switching among the three observation modes of the normal observation mode, the fluorescence observation mode and the deep blood vessel observation mode can be performed by pressing of the single switch SB. Therefore, according to the present embodiment, it is possible to reduce the burden on a surgeon who performs an operation while switching among the normal observation and the plurality of special light observations including the fluorescence observation.

Note that, in the present embodiment, for example, the controlling portion 45 may be adapted to, when the observation mode of the living body observation system 1 is set to the normal observation mode, generate a system control signal for causing WL light and IR light in the predetermined light amount PA to be generated by time division or alternately and output the system control signal to the light source controlling portion 34, and, while causing a fluorescent image generated based on an image pickup signal outputted from the endoscope 2 to be outputted to the judging portion 44, to generate a system control signal for causing a normal observation image generated based on an image pickup signal outputted from the endoscope 2 to be outputted to the display apparatus 5 and output the system control signal to the image generating portion 42. According to such an operation of the controlling portion 45, when the observation mode of the living body observation system 1 is set to the normal observation mode, it is possible to, while causing a normal observation image to be displayed on the display apparatus 5 as an observation image, cause the process for acquisition of the predetermined parameter by the judging portion 44 and the judgment process based on the predetermined parameter to be continuously performed in the background.

In the present embodiment, for example, the judging portion 44 may be adapted to acquire the number of pixels with a brightness value equal to or above a predetermined brightness value PB that are included in a fluorescence image outputted from the image generating portion 42 during the period until the predetermined time period PT elapses after the operation of step S3 of FIG. 6 is started, as the predetermined parameter corresponding to the light amount of FL light (fluorescence) emitted from the fluorescent medical agent administered to the subject, and to perform a judgment process according to the acquired number of pixels. The controlling portion 45 may be adapted to, in such a case, for example, set the observation mode of the living body observation system 1 to the fluorescence observation mode if a judgment result that the number of pixels with a brightness value equal to or above the predetermined brightness value PB is equal to or above a predetermined threshold THB is obtained, and set the observation mode of the living body observation system 1 to the deep blood vessel observation mode if a judgment result that the number of pixels with a brightness value equal to above the predetermined brightness value PB is below the predetermined threshold THB is obtained. Alternatively, the controlling portion 45 may be adapted to, in the case as described above, for example, set the observation mode of the living body observation system 1 to the fluorescence observation mode if a judgment result that there is one or more pixels with a brightness value equal to or above the predetermined brightness value PB is obtained, and set the observation mode of the living body observation system 1 to the deep blood vessel observation mode if a judgment result that a pixel with a brightness value equal to or above the predetermined brightness value PB does not exist is obtained.

Figure 7:
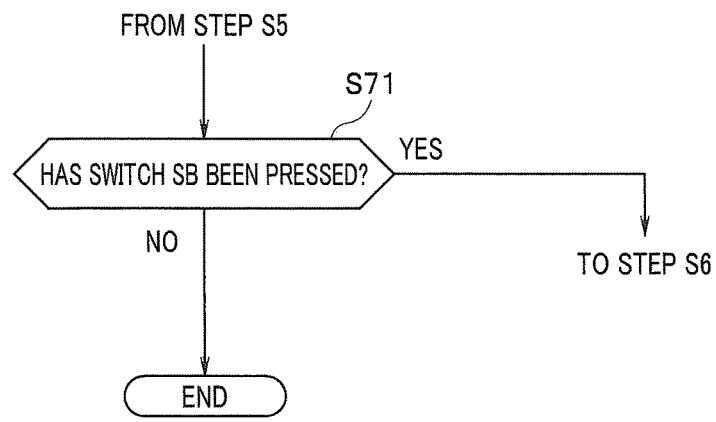
FIG. 7 is a diagram for illustrating an example of an operation performed in addition to the operation of FIG. 6.

The controlling portion 45 of the present embodiment may further perform, after completing the operation of step S5 of FIG. 6, for example, an operation of step S71 of FIG. 7. A specific example of such an operation of the controlling portion 45 will be described below. Hereinafter, specific description about a part to which a component, an operation or the like already described can be applied will be appropriately omitted for simplification. FIG. 7 is a diagram for illustrating an example of an operation performed in addition to the operation of FIG. 6.

After completing the operation of step S5 of FIG. 6, that is, after setting the observation mode of the living body observation system 1 to the fluorescence observation mode, the controlling portion 45 performs the operation for detecting the instruction in response to pressing of the switch SB (step S71 of FIG. 7).

If the controlling portion 45 cannot detect the instruction in response to pressing of the switch SB at step S71 of FIG. 7 (S71: NO), the controlling portion 45 maintains the fluorescence observation mode set by the operation of step S5 of FIG. 6. If the controlling portion 45 can detect the instruction in response to pressing of the switch SB at step S71 of FIG. 7 (S71: YES), the controlling portion 45 subsequently performs an operation similar to step S6 of FIG. 6.

Then, if the operation of step S71 of FIG. 7 as described above is performed, the observation mode of the living body observation system 1 can be switched from the fluorescence observation mode to the deep blood vessel observation mode, for example, at a desired timing before fluorescence emitted from the fluorescent medical agent administered to the subject completely fades away.

Figure 8:
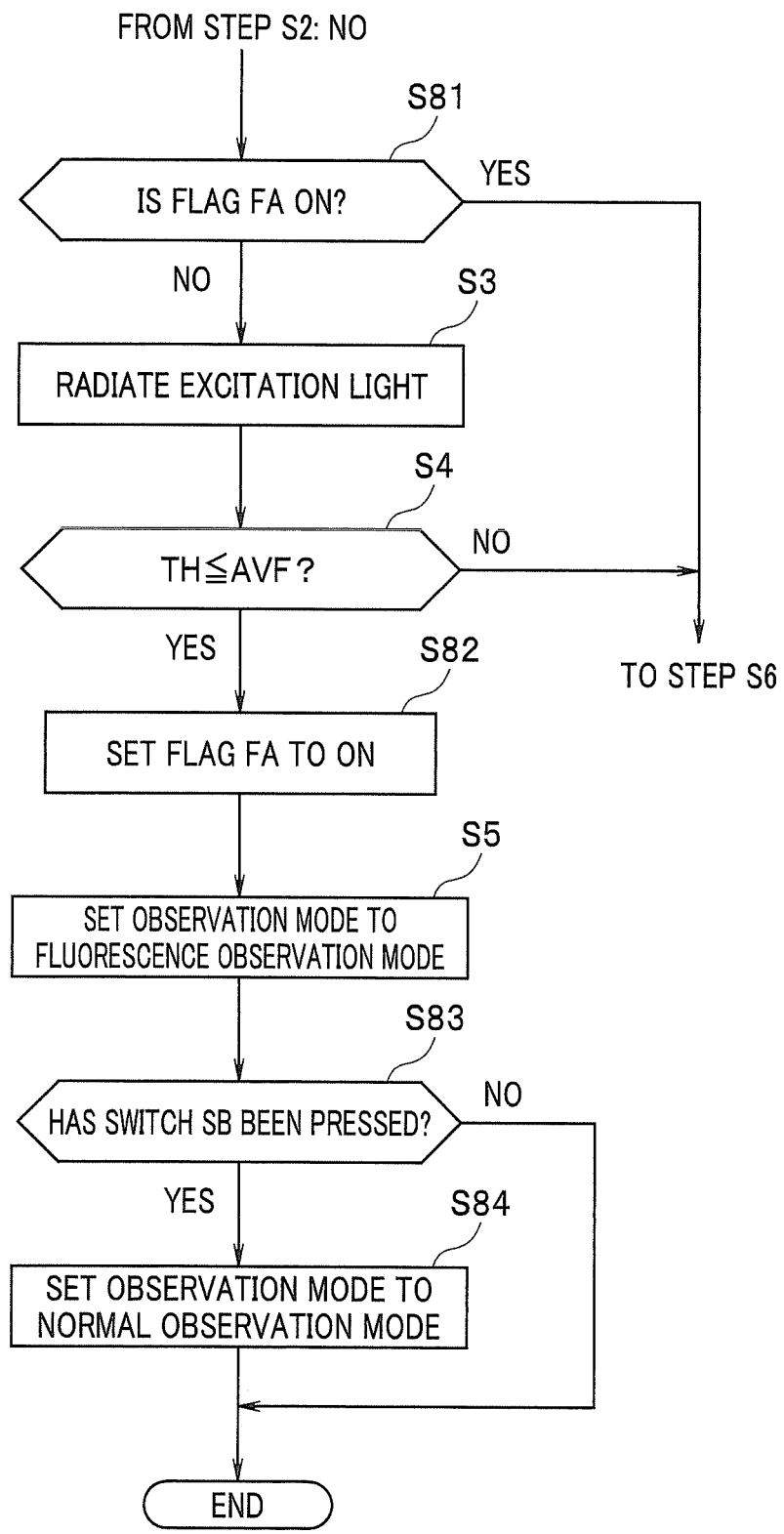
FIG. 8 is a diagram for illustrating an example of the operation performed in addition to the operation of FIG. 6.

For example, the controlling portion 45 of the present embodiment may further perform operations of steps S81 to S84 of FIG. 8 in the series of operations of FIG. 6. A specific example of such an operation of the controlling portion 45 will be described below. FIG. 8 is a diagram for illustrating an example of the operation performed in addition to the operation of FIG. 6.

If the controlling portion 45 obtains the judgment result that the observation mode set currently is not the deep blood vessel observation mode by the judgment process of step S2 of FIG. 6, the controlling portion 45 further performs a judgment process about whether a flag FA is on or not (step S81 of FIG. 8).

Note that it is assumed that the flag FA is, for example, information or a value stored in a not-shown memory provided in the processor 4. It is assumed that the flag FA is, for example, set to off immediately after the switch SA is pressed (that is, before the operation of step S1 of FIG. 6 is performed) and is set to on if the operation for switching the observation mode of the living body observation system 1 to the fluorescence observation mode is performed.

If the controlling portion 45 obtains a judgment result that the flag FA is off, by the judgment process of step S81 of FIG. 8 (S81: NO), the controlling portion 45 subsequently performs an operation similar to step S3 of FIG. 6. If the controlling portion 45 obtains a judgment result that the flag FA is on, by the judgment process of step S81 of FIG. 8 (S81: YES), the controlling portion 45 subsequently performs an operation similar to step S6 of FIG. 6. That is, according to such an operation of the controlling portion 45, for example, if, after switching from the normal observation mode to the fluorescence observation mode is performed in response to pressing of the switch SB, the switch SB is pressed again in the normal observation mode, the observation mode of the living body observation system 1 switches to the deep blood vessel observation mode irrespective of the predetermined parameter corresponding to the light amount of fluorescence.

If a judgment result that the average brightness value AVF is equal to or above the predetermined threshold THA is obtained, based on a judgment result outputted from the judging portion 44 after step S4 of FIG. 6 (S4: YES), the controlling portion 45 sets the flag FA to on (step S82 of FIG. 8) and after that, subsequently performs an operation similar to step S5 of FIG. 6. If a judgment result that the average brightness value AVF is below the predetermined threshold THA is obtained, based on a judgment result outputted from the judging portion 44 after step S4 of FIG. 6 (S4: NO), the controlling portion 45 subsequently performs an operation similar to step S6 of FIG. 6.

After completing the operation of step S5 of FIG. 6, that is, after setting the flag FA to on and setting the observation mode of the living body observation system 1 to the fluorescence observation mode, the controlling portion 45 performs the operation for detecting the instruction in response to pressing of the switch SB (step S83 of FIG. 8).

If the controlling portion 45 cannot detect the instruction in response to pressing of the switch SB at step S83 of FIG. 8 (S83: NO), the controlling portion 45 maintains the fluorescence observation mode set by the operation of step S5 of FIG. 6. If the instruction in response to pressing of the switch SB can be detected at step S83 of FIG. 8 (S83: YES), the controlling portion 45 sets the observation mode of the living body observation system 1 to the normal observation mode (step S84 of FIG. 8), generates a system control signal for causing the operation corresponding to the normal observation mode to be performed, and outputs the generated system control signal to the light source controlling portion 34, the image pickup device driving portion 41 and the image generating portion 42.

That is, according to the operation as described above, when the controlling portion 45 detects that the instruction in response to pressing of the switch SB is given after performing switching from the normal observation mode to the fluorescence observation mode, the controlling portion 45 switches the current observation mode to either the normal observation mode or the deep blood vessel observation mode.

If the operations of steps S81 to S84 of FIG. 8 as described above are performed, the number of times of switching from the normal observation mode to the fluorescence observation mode during the period until the switch SC is pressed after the switch SA is pressed is limited to one. Therefore, the observation mode of the living body observation system 1 can be efficiently switched in response to pressing of the switch SB.

Figure 9:
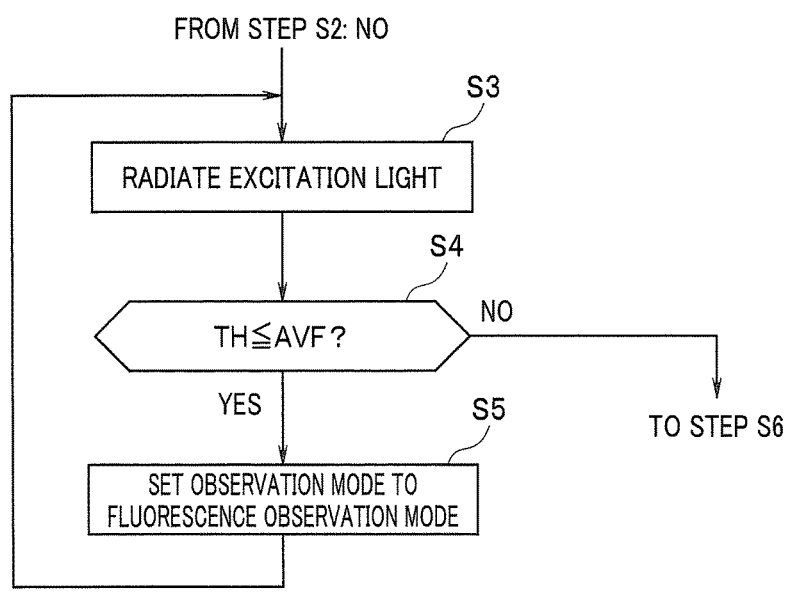
FIG. 9 is a diagram for illustrating an example of a case where a part of the operation of FIG. 6 is changed.

According to the present embodiment, for example, as shown in FIG. 9, the operations of steps S3 and S4 of FIG. 6 may be performed each time a predetermined period elapses after the controlling portion 45 completes the operation of step S5 of FIG. 6. FIG. 9 is a diagram for illustrating an example of a case where a part of the operation of FIG. 6 is changed.

In other words, the controlling portion 45 of the present embodiment may be adapted to, when setting the observation mode of the living body observation system 1 to the fluorescence observation mode, maintain the fluorescence observation mode if a judgment result showing that observation of FL light emitted from the fluorescent medical agent administered to the subject is possible is obtained based on a judgment result obtained by the judging portion 44, and to perform the operation for switching to the deep blood vessel observation mode if a judgment result showing that observation of the FL light is impossible is obtained.

Then, if the operation as described above is performed, the observation mode of the living body observation system 1 can be switched from the fluorescence observation mode to the deep blood vessel observation mode, for example, even if the instruction in response to pressing of the switch SB is not given when fluorescence emitted from the fluorescent medical agent administered to the subject completely fades away.

The present invention is not limited to the embodiment described above, and it goes without saying that various alterations and applications are possible within a range not departing from the spirit of the invention.

What is claimed is:
1. A living body observation system comprising:
   a light source apparatus capable of generating white observation light for acquiring a white observation image of a subject and excitation light for exciting fluorescent medical agent administered to the subject as illumination light for illuminating the subject;
   a camera unit configured to pick up an image of the subject that the illumination light is radiated to;
   a switch for giving an instruction to switch an observation mode at a time of observing the subject to any one observation mode among a normal observation mode to display the white observation image as an observation image and a plurality of special light observation modes including a fluorescence observation mode to display an observation image generated using a fluorescent image of the subject; and a processor including hardware; wherein
the processor is configured to:
generate a white observation image of the subject that the white observation light is radiated to, the white observation image being picked up by the camera unit, and the fluorescent image of the subject that the excitation light is radiated to, the fluorescent image being picked up by the camera unit;
acquire a parameter corresponding to a light amount of fluorescence emitted from the fluorescent medical agent based on the fluorescent image and judge whether or not the parameter meets a condition under which observation of the fluorescence is possible; and
when the processor detects that the instruction is given in the normal observation mode, perform an operation for switching to the fluorescence observation mode if the processor judges that the parameter meets the condition under which observation of the fluorescence is possible, and perform an operation for switching to a predetermined observation mode different from the fluorescence observation mode, among the plurality of special light observation modes, if the processor judges that the parameter does not meet the condition under which observation of the fluorescence is possible.

2. The living body observation system according to claim 1, wherein when the processor detects that the instruction is given in the fluorescence observation mode, the processor performs the operation for switching to the predetermined observation mode.

3. The living body observation system according to claim 1, wherein when the processor detects that the instruction is given after performing switching from the normal observation mode to the fluorescence observation mode, the processor performs an operation for switching a current observation mode to either the normal observation mode or the predetermined observation mode.

4. The living body observation system according to claim 1, wherein when the processor detects that, after performing switching from the normal observation mode to the fluorescence observation mode, switching to the normal observation mode is further performed, and the instruction is given in the normal observation mode, the processor performs an operation for switching the current observation mode from the normal observation mode to the predetermined observation mode not depending on the parameter.

5. The living body observation system according to claim 1, wherein the processor maintains the fluorescence observation mode if the processor judges that the condition under which observation of the fluorescence is possible is met, in the fluorescence observation mode, and performs the operation for switching to the predetermined observation mode if the processor judges that the condition under which observation of the fluorescence is possible is not met.

6. The living body observation system according to claim 1, wherein when the processor detects that the instruction is given in the normal observation mode or in the fluorescence observation mode, the processor performs an operation for causing a predetermined light amount of the excitation light to be radiated during a predetermined time period.

7. The living body observation system according to claim 1, wherein
the processor acquires an average brightness value of the fluorescent image as the parameter, and performs a judgment process for judging whether or not the average brightness value is equal to or above a predetermined threshold;
if the processor judges that the parameter is equal to or above the predetermined threshold, the processor performs the operation for switching to the fluorescence observation mode; and
if the processor judges that the parameter is below the predetermined threshold, the processor performs the operation for switching to the predetermined observation mode different from the fluorescence observation mode, among the plurality of special light observation modes.

8. The living body observation system according to claim 1, wherein
the processor acquires a number of pixels with a brightness value equal to or above a predetermined brightness value that are included in the fluorescent image as the parameter, and performs a judgment process for judging whether or not the number of pixels is equal to or above a predetermined threshold;
if the processor judges that the parameter is equal to or above the predetermined threshold, the processor performs the operation for switching to the fluorescence observation mode; and
if the processor judges that the parameter is below the predetermined threshold, the processor performs the operation for switching to the predetermined observation mode different from the fluorescence observation mode, among the plurality of special light observation modes.

9. The living body observation system according to claim 1, wherein the special light observation modes are observation modes making it possible to, by radiating special light, which is light band-limited according to characteristics of a predetermined target object in the subject, cause an image in which the predetermined target object is emphasized to be displayed.

* * * * *